(12) United States Patent
Eriksen et al.

(10) Patent No.: US 8,414,866 B2
(45) Date of Patent: Apr. 9, 2013

(54) METHOD OF MAGNETIC RESONANCE IMAGING OF THE HEART WITH PARAMAGNETIC MN$^{2+}$

(75) Inventors: Morten Eriksen, Oslo (NO); Geir Torheim, Oslo (NO)

(73) Assignee: GE Healthcare AS, Oslo (NO)

( * ) Notice: Subject to any disclaimer, the term of this patent is extended or adjusted under 35 U.S.C. 154(b) by 758 days.

(21) Appl. No.: 12/335,567

(22) Filed: Dec. 16, 2008

(65) Prior Publication Data

US 2009/0155184 A1   Jun. 18, 2009

(30) Foreign Application Priority Data

Dec. 17, 2007 (NO) .................................. 20076471
Dec. 17, 2007 (NO) .................................. 20076472

(51) Int. Cl.
   *A61B 5/055* (2006.01)
(52) U.S. Cl.
   USPC ...... 424/9.361; 424/1.61; 424/9.3; 424/9.323

(58) Field of Classification Search ................ 424/9.361
   See application file for complete search history.

(56) References Cited

U.S. PATENT DOCUMENTS 5,980,863 A * 11/1999 Harnish et al. ............... 424/9.36
7,966,056 B2 * 6/2011 Rongved et al. ............. 600/420

FOREIGN PATENT DOCUMENTS

| WO | 2004054623 | 7/2004 |
| WO | 2006028380 | 3/2006 |
| WO | WO 2006028380 A1 * | 3/2006 |

OTHER PUBLICATIONS

Nordhoy et al. NMR Biomed. 2003 16:82-95.*
Fletcher et al. Circulation. 2001 104: 1694-1740.*

* cited by examiner

*Primary Examiner* — Michael G Hartley
*Assistant Examiner* — Sean R Donohue
(74) *Attorney, Agent, or Firm* — Yonggang Ji

(57) ABSTRACT

The present invention relates to a magnetic resonance imaging (MRI) method, in particular to a MRI method enabling early detection of myocardial ischemia.

16 Claims, No Drawings

METHOD OF MAGNETIC RESONANCE IMAGING OF THE HEART WITH PARAMAGNETIC $MN^{2+}$

FIELD OF THE INVENTION

The present invention relates to a magnetic resonance imaging (MRI) method, in particular to a MRI method enabling early detection of myocardial ischemia.

The method of the invention is preferably used to detect and identify ischemic heart diseases as angina pectoris, myocardial infarction, myocardial stunning and hibernation or post ischemic heart failure, or any other form of heart failure and heart disease.

BACKGROUND OF THE INVENTION

Ischemia-related diseases, in particular coronary artery diseases, account for the majority of deaths in the Western countries. Myocardial ischemia is a serious condition and rapid identification and location of myocardial ischemia is therefore highly desirable so that the necessary actions, e.g. therapeutic or surgical treatment, can be taken promptly before irreversible myocardial damage occurs.

Ischemic injury can be considered to result from two main events: (i) hypoxia leading to an inadequate supply of oxygen to the tissues; and (ii) decreased transport of metabolic substrates to the tissues and of metabolic end products from the tissues. Immediate consequences include energy deficit and an accumulation of protons and lactate in the region of ischemia. Other consequences include a marked, potentially harmful stimulation of the sympathetic nervous system, which ultimately leads to a rapid loss of adenosine triphosphate (ATP), an early onset of acidosis and decreased organ function.

Cardiac tissue, like other metabolically active tissues, is particularly vulnerable to ischemic injury. The initial phase of acute myocardial infarction is in general associated with a loss of normal contractile function, which manifests itself as regional dyskinesia. This may be due to an abrupt fall in coronary perfusion pressure, which induces an acute hibernating state, and to the rapid cessation of normal trans-membrane ion transport. Reperfusion of the ischemic myocardium prior to the onset of irreversible injury may lead to a rapid or delayed return (stunning) to normal cardiac metabolism and function.

Magnetic resonance imaging (MRI) has been established as a useful cardiac imaging technique. Although MR techniques using spin-echo imaging are capable of showing the anatomy of the heart, the use of contrast agents is necessary for the detection of myocardial ischemia and infarction. One class of MR contrast agents is paramagnetic contrast agents, which comprise a paramagnetic metal ion, preferably $Mn^{2+}$ ion in the form of a salt or in a complex with a chelating/complexing moiety.

By intravenous infusion of a manganese contrast agent that releases divalent and paramagnetic $Mn^{2+}$ ions, these ions will be easily taken up into cardiac cells and act as intracellular contrast agents. Cell uptake of $Mn^{2+}$ ions occur via physiological channels in the cell membrane for calcium ($Ca^{2+}$) ions which are main conductors of cell physiology and metabolism. The intracellular $Mn^{2+}$ ion retention lasts for hours and $Mn^{2+}$ ions induce paramagnetic effects inside the cardiac cell.

The total influx of $Mn^{2+}$ ions per time unit is raised during increased heart rate and force of contraction. However, in ischemic myocardium, much less $Mn^{2+}$ ions are taken up because of reduction in blood flow, mitochondrial function and metabolism and decrease in contractility. Hence ischemic myocardium can be detected and distinguished from normal myocardial tissue by MR imaging using paramagnetic $Mn^{2+}$ ions as a contrast agent. Further, $Mn^{2+}$ is not a substrate for $Ca^{2+}$ ATPase and the $Na^+/Ca^{2+}$ exchanger during relaxation, and is hence retained in the heart for many hours. This "memory effect" lasts long enough to perform MR investigation in such a way, that a patient administered with a $Mn^{2+}$ comprising contrast agent performs physical exercise outside the MR imager to raise heart rate and subsequent imaging is then performed up to 1 hour after administration. Another reason for using a regimen of stress is that it allows for lower doses of the contrast agent.

According to prior art, contrast agents are administered to the body before, simultaneously with or after stress. By stress is meant raising the heart rate and myocardial metabolism physically and/or pharmacologically to a maximum level, also called peak stress. After the stress procedure is completed, the body is subjected to an imaging procedure.

WO A1 2004/054623 describes a method of MR imaging where contrast agent is administered to the body and a regimen of physical and/or pharmacological stress is exposed to the body before or simultaneously to the contrast agent administration.

WO A1 2006/028380 describes a two step method and a one step method of MR imaging.

In both procedures the contrast agent should be administered to the body by slow intravenous infusion. In the two-step method the patient is exposed to stress after infusion of the contrast agent, and in the one step method stress and infusion is performed simultaneously.

SUMMARY OF THE INVENTION

By increasing the heart rate and force of contraction uptake of $Mn^{2+}$ ions into the cardiac cells is increased but the uptake into ischemic myocardium is limited, and the ischemic myocardium can be distinguished from normal myocardial tissue. There is still a need for further improvements of the MR technique, and it is an object of the present invention to provide a method that obtains high quality images from the imaging procedure.

This object is solved by the present invention by providing a method of MR imaging comprising administering a contrast agent comprising manganese ions ($Mn^{2+}$) to the human or non-human animal body and exposing said body to a regimen of physical and/or pharmacological stress simultaneously with and/or after the contrast agent administration, followed by the administering of a calcium solution to said body, and subjecting said body to an imaging procedure.

DETAILED DESCRIPTION OF THE INVENTION

According to prior art MRI procedures to detect cardiac disease comprises administration of a contrast agent comprising $Mn^{2+}$ ions to the human or non-human animal body, exposing said body to a regimen of physical and/or pharmacological stress and subjecting said body to an imaging procedure.

Applying stress ensures a difference in uptake of $Mn^{2+}$ ions in ischemic myocardium and normal myocardial tissue. After exposing the patient to stress the heart rate goes back to a normal level and a difference in uptake can no longer usually be observed. At this point there are still $Mn^{2+}$ ions in the blood pool which will be taken up into the cardiac cells. Since there will no longer be observed any differences in the uptake of these ions, this uptake will have a negative impact on the relative differences between ischemic myocardium and normal myocardial tissue established during the stress regimen. Considering this negative effect it would be desirable to limit the uptake of $Mn^{2+}$ ions into the cardiac cells at this point of time.

According to the present invention this is done by administering a calcium solution to said body. By administering a calcium solution to the body $Ca^{2+}$ ions will compete with $Mn^{2+}$ ions in entering the slow $Ca^{2+}$ channels leading to the myocardium. Hence more $Ca^{2+}$ ions are present to compete with $Mn^{2+}$ ions and less $Mn^{2+}$ ions are taken up into the cardiac cells.

Generally a MR procedure according to the present invention will comprise infusion of contrast agent to the body and exposing said body to stress in connection with the infusion, before and/or simultaneously with the stress procedure. After the regimen of stress has ended, a calcium solution is administering to the body. The body is then exposed to an imaging procedure.

In one embodiment the calcium solution can be administered to the body immediately after the regimen of physical and/or pharmacological stress is ended. This means that when the patient is subjected to physical stress the calcium solution is administered to the body immediately after the activity is ended, and when the patient is subjected to pharmacological stress the calcium solution is administered to the body immediately after the heart rate has started to drop.

In a preferred embodiment the calcium solution can be administered to the body immediately after the regimen of physical and/or pharmacological stress no longer has an impact on the heart rate, i.e. when the heart rate has returned to a normal level. In this way administration of calcium solution is separated from the high heart rate level generated from the regimen of stress and side effects from both interventions is reduced.

$Ca^{2+}$ ions can be administered to the body as a solution containing a soluble calcium compound. Preferably the solution is chosen from calcium chloride, calcium gluconate, calcium lactate and calcium aspartate, most preferably calcium chloride and calcium gluconate.

Solutions of the $Ca^{2+}$ ions for parenteral administration, e.g. intravenous administration, should be sterile and free from physiologically unacceptable agents, and should have low osmolality to minimize irritation or other adverse effects upon administration.

$Ca^{2+}$ ions can be administered to the body by bolus injection, although a slow intravenous injection or slow intravenous infusion is preferred. The calcium solution can be administered at a suitable dose, for example a dose of 50 μmol $Ca^{2+}$ ion/kg body weight, or more preferably 100 μmol $Ca^{2+}$ ion/kg, and most preferably 150 μmol $Ca^{2+}$ ion/kg. The rate at which the calcium solution is administered will depend on the concentration of the solution, and the total amount to be administered. Preferably the calcium containing solution is administered by slow infusion, preferably over a period of 5 to 30 minutes, and most preferably 10 to 20 minutes.

As described in prior art the stress regimen exposed to the patient according to the present invention can be peak stress, i.e. stressing the patient to the maximum level of what the body can tolerate. This implies that the patient is exposed to stress where the heart rate increases gradually until said maximal level where the patient is not able to be exposed to further stress, is reached. At this point the stress regimen is ended and the amount of contrast agent content in the cardiac cells is believed to be at the highest possible level and sufficient to obtain high quality images from the imaging procedure.

In a preferred embodiment the stress subjected to the patient is submaximal stress. By submaximal stress is meant a stress level that lies below the maximal level of stress that the patient's body can tolerate. A result of subjecting the patient to submaximal stress is it causes less discomfort to the patient than a stress regimen that is taken to peak stress, and it is safer causing a lower health risk to the patient.

Employing the method where the patient is subjected to submaximal stress can thus ensure a sufficient uptake of $Mn^{2+}$ ions and at the same time perform uptake in an efficient, safe and comfortable manner for the patient.

Applying stress ensures a higher uptake of $Mn^{2+}$ ions into the cardiac cells and also ensures a difference in uptake of $Mn^{2+}$ ions in ischemic myocardium and normal myocardial tissue. The total influx of $Mn^{2+}$ ions per time unit is raised during increased heart rate and force of contraction, hence the higher the heart rate the higher the uptake. Although subjecting the patient to peak stress will give a higher uptake of $Mn^{2+}$ ions per time unit, applying submaximal stress enables the patient to be exposed to stress over a longer period of time. Hence instead of using peak stress which ensures a higher uptake per time unit over a shorter period of time, according to the present invention one can use submaximal stress which ensures a lower uptake per time unit over a longer period of time resulting in a higher total uptake.

By submaximal stress is meant a stress level that lies below the maximal level of stress that the patient's body can tolerate. The heart rate during submaximal stress is always within a range from above the patient's resting heart rate (HRrest) to below the patient's age-dependent maximum heart rate (HRmax). The age dependent maximum heart rate is approximately 210 minus the patient's age in years. A suitable heart rate during submaximal stress can be calculated as:

$HR$submax$=(1-F)*HR$rest$+F*HR$max, where $F$ is between 0 (no stress) and 1 (maximum stress).

F can be varied from about 0.2 to 0.8, more preferably from 0.4 to 0.6 and most preferred F is 0.5.

Using the value F=0.5 for a patient aged 60 with a resting heart rate of 70, the heart rate during sub-maximal stress will be: $[(1-0.5)*70+0.5*(210-60)]=110$.

To achieve the highest possible uptake of contrast agent in each case one can adjust the level of submaximal stress, the length and number of stress periods.

Hence in one embodiment the submaximal regimen of stress can be exposed to the patient in one continuous period. By subjecting the patient to submaximal stress he or she can endure the regimen of stress continuously for a long enough period of time to give a high and sufficient uptake of contrast agent, generally a period of 5 to 30 minutes. Depending on the patients physical condition the uptake is optimised by the length and level of the submaximal stress regimen. A higher stress level requires a shorter time period but a lower stress level will enable the patient to endure stress for a longer period of time. Both procedures can result in the same total uptake of contrast agent but patients can have different preferences on the two procedures and will be able to choose which procedure is more preferable from a personal perspective.

When the regimen of stress is subjected to the patient in one continuous period the contrast agent can be administered to the body before and/or simultaneously with applying stress.

In a preferred embodiment the regimen of stress is exposed to the body simultaneously with the contrast agent administration and for the entire duration of the contrast agent administration. This ensures a maximal uptake of $Mn^{2+}$ ions to the cardiac cells.

In a further embodiment said regimen of stress exposed to said body continues after the administration of contrast agent has ended, i.e. stress is exposed to the body simultaneously with and after the contrast agent administration.

In certain situations the patient may not be able to endure even submaximal stress for a long enough period of time to ensure a sufficient uptake of contrast agent. Hence in a second embodiment of the present invention the regimen of stress can be divided into several intervals where the patient can lower the stress level between high level stress periods. In this way the patient can have periods of rest making him or her able to endure a total period of a high enough stress level in order to obtain a sufficient uptake of contrast agent. When the patient is exposed to physical stress he or she can lower the intensity of the activity between stress periods, and when the patient is exposed to pharmacological stress the patient can get doses of the stressor that gives shorter stress periods in several injections with resting periods in between. The contrast agent can be administered to the body before and/or simultaneously with the first stress period, or in smaller doses before and/or simultaneously with each stress period.

In yet other situations the patient may only endure submaximal stress for a very short period of time and he or she may need a period of total absence of stress before continuing with another stress period. Hence in a third embodiment of the present invention the regimen of stress can be divided into several intervals where the patient can rest in total absence of stress between the stress periods.

In this way the patient can have periods of complete rest making him or her able to endure a total period of a high enough stress level in order to obtain a sufficient uptake of contrast agent. When the patient is exposed to physical stress he or she can stop the activity completely between stress periods, and when the patient is exposed to pharmacological stress the patient can get doses of the pharmacological stressor that gives shorter stress periods in several injections with resting periods in between. The contrast agent can be administered to the body before and/or simultaneously with the first stress period, or in smaller doses before and/or simultaneously with each stress period.

In a particularly preferred embodiment the stress regimen is divided in two intervals with a resting period in between. Preferably the patient is exposed to the first stress regimen simultaneously with contrast agent administration, and after a resting period the patient is exposed to a second regimen of stress.

In yet further embodiments stress can be applied after administration of the contrast agent.

It may be advantageous to expose the regimen of stress to the body after the administration of contrast agent such that the contrast agent administration is separated from stress and side effects from both interventions can be greatly reduced. This also means that a patient can for example receive an intravenous infusion of contrast agent in a suitable location and thereafter receive a pharmacological stressor or undergo physical stress by exercise in a second location with good possibilities for patient monitoring and surveillance.

Stress can preferably be applied over a total period of 5 to 30 minutes, preferably 10 to 20 minutes. When stress is applied simultaneously with contrast agent administration and continuous after the administration of contrast agent has ended, the stress regimen can preferably be applied for an additional period of 5 to 20 minutes, preferably 10 to 15 minutes.

The stress according to the present invention is preferably a physical stress outside the magnet, e.g. exercise stress for example on a treadmill. Alternatively, pharmacological stress may be employed e.g. by the administration of pharmacological stressors. The pharmacological stressor can be any pharmaceutical agent that increases cardiac work or heart rate. For example the stressor can be an adrenergic agonist of both $\beta$ and $\alpha$ type, preferably $\beta$-adrenergic agonists like isoprenaline and dobutamine, or a cholinergic antagonist, preferably atropine.

In the method according to the present invention the contrast agent can be administered by a bolus injection although slow injection or infusion of the contrast agent is preferred. Preferably the contrast agent is administered by slow infusion over 5 to 30 minutes, preferably 10 to 20 minutes, avoiding or reducing potential side-effects.

Preferably, the contrast agents used in the method of the invention are administered at a dose of 0.1 to 30 $\mu$mol $Mn^{2+}$ ion/kg body weight, more preferably 0.5 to 30 $\mu$mol $Mn^{2+}$ ion/kg, most preferably 10 to 20 $\mu$mol $Mn^{2+}$ ion/kg.

Preferred complexing moieties in the complexes used in the method of the invention are low molecular weight hydrophilic complexing moieties. Examples of useful complexing agents are N,N'-bis-(pyridoxal-5-phosphate)ethylenediamine-N,N'-diacetic acid (DPDP), N,N'-bis-pyridoxal-ethylenediamine-N,N'-diacetic acid (PLED), diethylenetriamine-pentaacetic acid-bismethylamide (DTPABMA), ethylenediamine-tetraacetic acid-bismethylamide (EDTABMA) polyphosphates, and in particular triphosphate ($P_3O_{10}^{5-}$; TPP)) and 1,7-dicarboxy-2,6-bis(carboxymethyl)-4-hydroxy-2,6-diaza)-heptane (HPTA).

The complexes used in the method of the invention can be produced from commercially available complexing moieties or from complexing moieties described in the literature and oxides or acid salts such as chlorine and acetate salts of the paramagnetic metal for example as described in U.S. Pat. No. 4,647,447. The synthesis of MnDPDP is described in EP 0290047 B1. The synthesis of HPTA-complexes is described in U.S. Pat. No. 5,246,696. These documents are hereby included by reference. Briefly, the formation of the Mn complexes for use in the method of the invention involves dissolving or suspending manganese oxide or manganese salts like manganese chloride or manganese acetate in water or a lower alcohol like methanol, ethanol or isopropanol. To this solution or suspension is added an equimolar amount of the complexing moiety in water or a lower alcohol and the mixture is stirred, if necessary with heating, until the reaction is completed. If the complex formed is insoluble in the solvent used, the reaction product is conveniently isolated by filtering. If it is soluble, the reaction product is isolated by evaporating to dryness, e.g. by spray drying or lyophilising.

When these complexes are used in the MR contrast agents used in the method of the invention, the contrast agent formulation preferably comprises an antioxidant e.g. ascorbic acid or a reducing sugar to inhibit oxidation to $Mn^{3+}$ and $Mn^{4+}$ with subsequent precipitation of $MnO_2$. Providing the commercial contrast agent product in lyophilized form in an inert gas atmosphere, e.g. argon gas atmosphere, will stabilise the product during storage.

In a further preferred embodiment, the complexes used in the method according to the invention comprise $Mn^{2+}$ ions and a complexing moiety and further 0 to 2 mol $Ca^{2+}$ per mol $Mn^{2+}$, preferably 0.1 to 2 mol, more preferably 0.1 to 1.75 mol and most preferably 0.5 to 1 mol. Hence, a particularly preferred complex is CaMnHPTA containing 1 mol $Ca^{2+}$ per mol $Mn^{2+}$ and the preferred complexing moiety HPTA. Another particularly preferred contrast agent comprises $Z_2$MnHPTA, wherein Z is hydrogen or an alkali metal ion, preferably a sodium ion, and $Ca^{2+}$ with 0.5 mol $Ca^{2+}$ per mol $Mn^{2+}$. In a preferred embodiment, the complexes used in the inventive method are prepared from a mixture of $Ca^{2+}$ (e.g. in the form of a salt like calcium chloride) and $Mn^{2+}$ ions in the described molar ratio. In another preferred embodiment, the contrast agent is prepared by adding $Ca^{2+}$ (e.g. in the form of a salt like calcium chloride) to a $Mn^{2+}$ containing complex to obtain the described molar ratio.

For use in the method of the invention, the contrast agents comprising the complexes may further comprise conventional pharmaceutical or veterinary formulation aids, for example stabilisers, antioxidants, osmolality adjusting agents, buffers and pH adjusting agents. The contrast agents may be in a form suitable for injection or infusion directly or after dispersion in or dilution with a physiologically acceptable carrier medium, e.g. water for injections. Thus the contrast agents may be in a conventional pharmaceutical administration form such as a lyophilised product, a powder, a solution, a suspension, a dispersion, etc. However, solutions in physiologically acceptable carrier media will generally be preferred. Suitable additives include, for example, physiologically biocompatible buffers.

The contrast agent solutions should preferably be isotonic or slightly hypertonic. Suitable vehicles include aqueous vehicles customarily used for administering parenteral solutions such as Sodium Chloride Injection, Ringer's Injection, Dextrose Injection, Dextrose and Sodium Chloride Injection, Lactated Ringer's Injection and other solutions. Such vehicles are described in Remington's Pharmaceutical Sciences, 15th ed., Easton: Mack Publishing Co., pp. 1405-1412 and 1461-1487 (1975) and The National Formulary XIV, 14th ed. Washington: American Pharmaceutical Association (1975).

Solutions of the contrast agent may further contain preservatives, antimicrobial agents, buffers and antioxidants conventionally used for parenteral solutions. Excipients and other additives which are compatible with the complexes and which will not interfere with the manufacture, storage or use of the products may also be employed.

In a preferred embodiment the contrast agent is Teslascan™, an isotonic contrast agent available as a ready-to-use formulation provided by GE Healthcare.

Preferably the body is subjected to MR imaging after a time period sufficient for the MR signal intensity of the blood pool to become insignificantly different from the precontrast baseline signal intensity. More preferably, the body is subjected to MR imaging after a time period of at least 5 minutes from the administration of the contrast agent, more preferably within a period of 10 to 60 minutes, even more preferably within a period of 10 to 45 minutes and most preferably within a period of 15 to 30 minutes after contrast agent administration.

Highly $T_1$-sensitive, fast or ultra-fast imaging techniques which enable the generation of a series of images with a time interval as short as possible between successive images are preferred. MR imaging techniques capable of generating images with time intervals of less than 100 milliseconds are particularly preferred. Thus MR imaging techniques suitable in the method of the invention include gradient echo and echo planar imaging, especially inversion recovery echo planar imaging, e.g. gradient refocused inversion recovery echo planar imaging. Particularly suitable echo planar imaging techniques are those in which TI (inversion time) is 100 to 800 milliseconds, TR (repetition time) corresponds to the heart rate and TE (echo time) is less than 20 milliseconds, e.g. 10-20 milliseconds. The sensitivity of the imaging technique may be increased by gating to every heartbeat. Flip angles for use in the preparation interval preceding image data acquisition may either be 180° or 90°, with 90° being preferred. Using a flip angle of 90° it is preferable to acquire single heart beat temporal resolution.

Example 1 shows a method according to prior art and example 2 shows a possible way of carrying out the methods of the present invention.

EXAMPLE 1

Prior Art

A patient with a 50% coronary stenosis is given an infusion of mangafodipir 0.01 mmol/ml (Teslascan™) at a rate of 5 ml/min over a time period of 10 minutes. After 5 minutes, a gradually increasing treadmill exercise is started, reaching the patient's maximum exercise capacity after 5 minutes, at the same instance as the infusion ends. 15 minutes later, a T1 weighted image of the patient's heart is made with an MRI scanner. The signal intensity from normal and ischemic myocardium is read from the images.

EXAMPLE 2

The same patient as in Example 1 is given an infusion of mangafodipir 0.01 mmol/ml (Teslascan™) at a rate of 5 ml/min over a time period of 10 minutes. After 5 minutes, a gradually increasing treadmill exercise is started, reaching the patient's maximum exercise capacity after 5 minutes, at the same instance as the infusion ends. An intravenous infusion of 0.1 mmol/ml calcium chloride given at a rate of 10 ml/min is started immediately after ending the exercise, and is continued for 15 minutes. The patient's heart is then imaged with MRI as described in Example 1. The signal intensity from normal and ischemic myocardium is read from the images.

SPECIFIC EMBODIMENTS, CITATION OF REFERENCES

The present invention is not to be limited in scope by specific embodiments described herein. Indeed, various modifications of the inventions in addition to those described herein will become apparent to those skilled in the art from the foregoing description. Such modifications are intended to fall within the scope of the appended claims.

Various publications and patent applications are cited herein, the disclosures of which are incorporated by reference in their entireties.

What is claimed is:

1. Method of MR imaging comprising administering a contrast agent comprising manganese ($Mn^{2+}$) to the human or non-human animal body before and/or simultaneously with exposing said body to a regimen of physical and/or pharmacological stress, and subjecting said body to an imaging procedure, characterized in that a calcium solution is administered by slow infusion over a period of 10 to 20 minutes to said body after the regimen of physical and/or pharmacological stress and prior to said imaging procedure.

2. Method according to claim 1, wherein said calcium solution is administered to said body immediately after the regimen of physical and/or pharmacological stress has ended.

3. Method according to claim 1, wherein said calcium solution is administered to said body immediately after the heart rate has returned to a normal level.

4. Method according to claim 1, wherein the calcium solution is chosen from calcium chloride, calcium gluconate, calcium lactate and calcium aspartate.

5. Method according to claim 1, wherein the calcium solution is administered at dose of 150 μmol calcium ion/kg.

6. Method according to claim 1 wherein said physical and/or pharmacological stress is submaximal.

7. Method according to claim 6, wherein said submaximal stress denotes a heart rate, HRsubmax, calculated as $$HR\text{submax}=(1-F)*HR\text{rest}+F*HR\text{max}$$

where HRrest is the patient's resting heart rate, HRmax is the patient's age-dependent maximum heart rate and F can be varied from about 0.2 to 0.8, more preferably from about 0.4 to 0.6 and most preferred F is 0.5.

8. Method according to claim 1, wherein said regimen of physical and/or pharmacological stress is divided in several intervals.

9. Method according to claim 1, wherein said regimen of stress is exposed to the body by controlled physical exercise or by infusion of a pharmacological stressor.

10. Method according to claim 1, wherein said pharmacological stressor is any pharmaceutical agent that increases cardiac work or heart rate.

11. Method according to claim 9, wherein said pharmacological stressor is an adrenergic agonist or a cholinergic antagonist.

12. Method according to claim 1, wherein said contrast agent is administered to said body by slow infusion.

13. Method according to claim 1, wherein said contrast agent is mangafodipir.

14. Method according to claim 11, wherein said pharmacological stressor is dobutamine or isoprenaline.

15. Method according to claim 11, wherein said pharmacological stressor is atropine.

16. Method according to claim 12, wherein said contrast agent is administered to said body by slow infusion over a period of 10 to 20 minutes.

* * * * *